US00PP35865P3

(12) United States Plant Patent
Olesen et al.

(10) Patent No.: US PP35,865 P3
(45) Date of Patent: Jun. 11, 2024

(54) *CLEMATIS* PLANT NAMED 'EVIPO116'

(50) Latin Name: *Clematis viticella*
Varietal Denomination: Evipo116

(71) Applicants: Mogens Nyegaard Olesen, Fredensborg (DK); Raymond J. Evison, Braye Vineries Guernsey (GB)

(72) Inventors: Mogens Nyegaard Olesen, Fredensborg (DK); Raymond J. Evison, Braye Vineries Guernsey (GB)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/445,490

(22) Filed: Sep. 8, 2023

(65) Prior Publication Data

US 2024/0107928 P1 Mar. 28, 2024

(30) Foreign Application Priority Data

Sep. 30, 2022 (QZ) ..... PBR 2022/2180

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
CPC ..... A01H 5/02
See application file for complete search history.

(56) References Cited

PUBLICATIONS https://issuu.com/nolinakwekerijen/docs/voorbeeld_nolina_brochure_2510; 2020; 1 page.*
https://www.ballcolegrave.co.uk/PdfAssets/pdfpage.aspx?pdfid=1689; 2021; 2 pages.*
https://www.pressreader.com/uk/yours-uk/20210406/285739886777221; Apr. 6, 2021; 1 page.*

* cited by examiner

*Primary Examiner* — Kent L Bell

(57) ABSTRACT

A new *Clematis* plant with a compact growth habit, profuse, light pink flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical Classification:
Genus: *Clematis.*
Species: *viticella.*
Variety denomination: 'Evipo116'.

This application claims priority to Plant Breeder's Rights Application Number 2022/2180, which was filed at the Community Plant Variety Rights Office in the European Union on Sep. 30, 2022, the contents of which are hereby incorporated by reference for all purposes.

SUMMARY OF THE CLAIMED PLANT

The present invention constitutes a new and distinct variety of *Clematis* plant which originated from a controlled crossing between the female seed parent, an un- named seedling, and the male pollen parent, an un-named seedling. Both parent varieties are non-patented.

The two parents were crossed during the summer of 2005 and the resulting seeds were planted the following winter in a controlled environment in Guernsey, Channel Islands, United Kingdom. The new variety named 'Evipo116' originated as a single seedling from the stated cross.

The new *Clematis* plant may be distinguished from its female seed parent and male pollen parent by the following characteristics. The female seed parent has mauve tepals while the new variety has light pink tepals. The female seed parent grows to a height of 35 cm in a single growing season while the new variety grows to a height of about 100 cm in one growing season. The male seed parent has light pink tepals about 50 mm in length while the new variety has light pink tepals about 55 mm in length. The male seed parent has a central bar running the length of tepals Purple-Violet Group 81A in color, while the claimed plant has a similar central bar the color of Purple Group 75A.

The objective of the hybridization of this *Clematis* plant was to create a new and distinct variety for nursery culture with unique qualities such as:

1. Uniform and abundant light pink flowers;
2. Vigorous and compact growth, making the variety suitable for container culture;
3. Improved disease resistance; and
4. Flowering heavily from new growth.

This combination of qualities was lacking in *Clematis* plants that were in commercial cultivation and the qualities have been substantially achieved in the new variety.

'Evipo116' was selected by Mogens N. Olesen and Raymond J. Evison in their *Clematis* development program in the Channel Islands, United Kingdom in 2006. Asexual reproduction of 'Evipo116' by means of vegetative cuttings and traditional layering was first performed by Mogens N. Olesen and Raymond J. Evison in the nursery located in Guernsey UK during the summer of 2006. This initial and subsequent asexual propagations have demonstrated that the characteristics of 'Evipo116' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo116'.

Specifically illustrated in FIG. 1 of the drawings are an open flower viewed from above, tepals detached revealing reproductive flower parts, a flower bud, and a side view of flowers at various stages of opening.

DETAILED DESCRIPTION OF THE VARIETY

Figure 1:
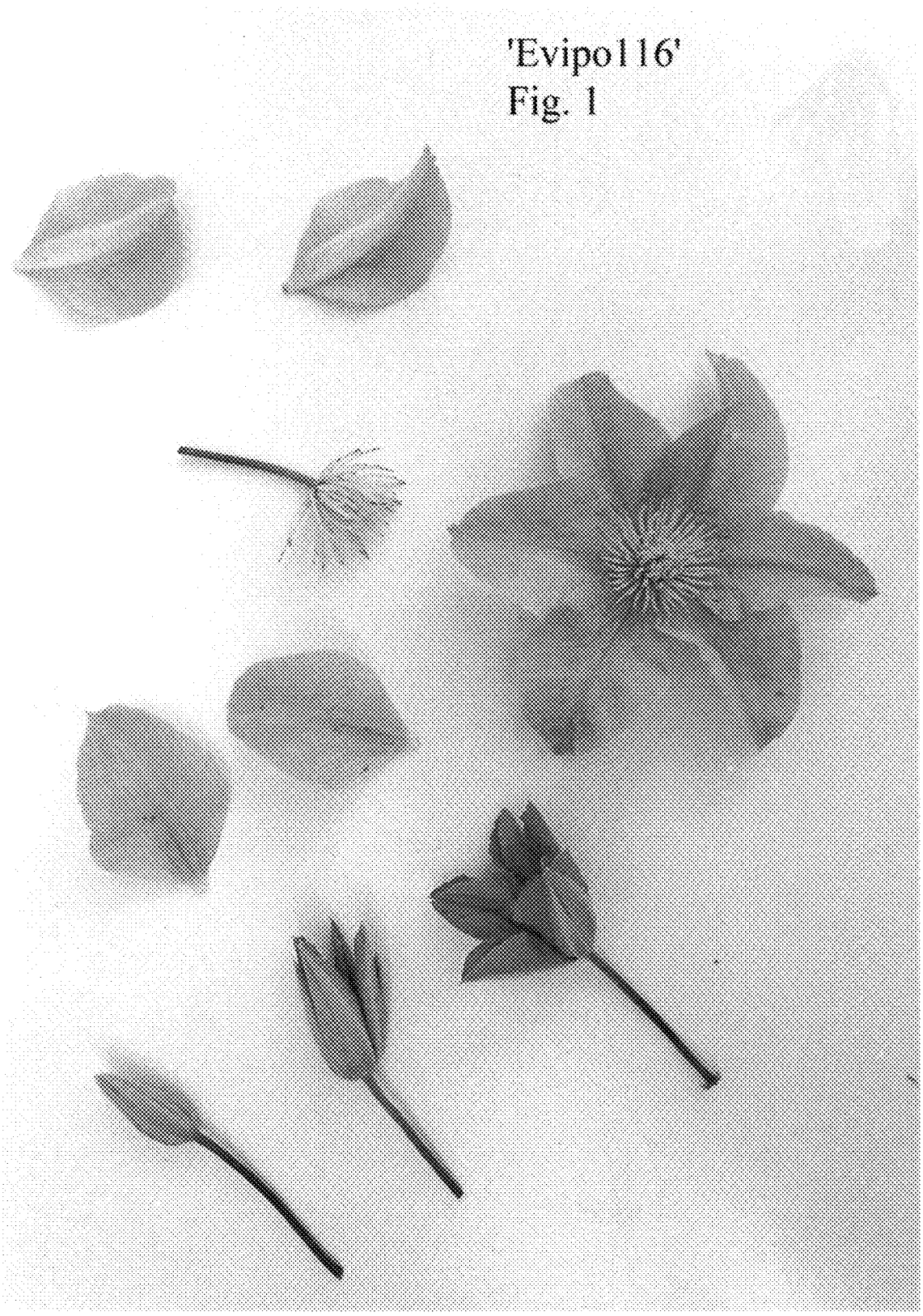
Figure 2:
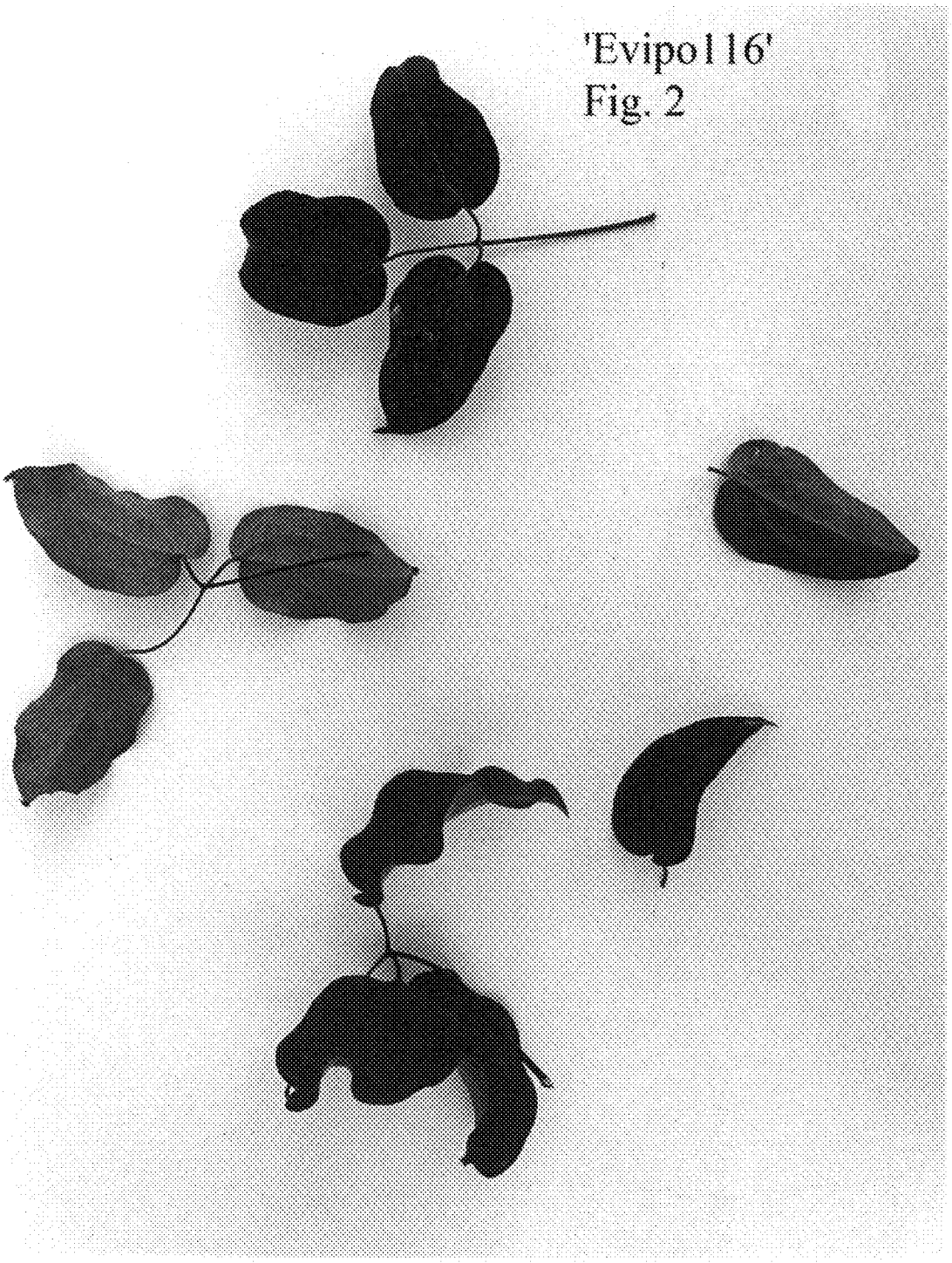
FIG. 2 shows mature leaves, leaflets, petioles, and petioloules. Illustrated plants are 2 years of age.

The following is a detailed description of 'Evipo116', as observed in its growth throughout the flowering period in Odense Denmark. Observed plants were cultivated outdoor for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *Clematis* variety 'Evipo056' described and illustrated in U.S. Plant Pat. No. 27,279 are compared to 'Evipo116'. While 'Evipo116' has a tepal colour of Purple Group 75B, 'Evipo056' has a tepal colour of Purple-Violet Group 82C. Styles in the reproductive flower parts on the claimed plant are Green Yellow Group 8D, while styles of 'Evipo056' are Yellow-Green Group 144B. Flower bud length of 'Evipo116' is 30 mm, while flower bud length for 'Evipo056' is 20 mm.

FLOWER AND FLOWER BUD

Blooming habit: Continuous. The natural flowering period is generally from April to September.

Flower bud:
- *Size*.—Normally 30 mm in length. Bud diameter is 10 mm.
- *Bud form*.—Long campanulate, broad based.
- *Bud color*.—Yellow-Green Group 145D.
- *Texture*.—Pubescent.

Pedicel:
- *Surface texture*.—Smooth.
- *Length*.—On average 50 mm in length with 2 mm diameter.
- *Color*.—Yellow-Green Group 144C with intonations of Greyed-Orange Group 166A.
- *Strength*.—Moderately strong.

Receptacle:
- *Surface texture*.—Lightly pubescent.
- *Shape*.—Broad funnel.
- *Size*.—1 mm (h)×1 mm (w).
- *Color*.—Yellow-Green Group 144A.

Flower arrangement:
- *Location on vine*.—New growth.
- *Borne*.—Normally in clusters of 7 to 10 flowers on a branch.

Flower bloom:
- *Size*.—On average, flowers are 100 mm in diameter and 20 mm in depth.
- *Profile*.—Open flowers are flat.
- *Fragrance*.—None.
- *Lasting quality*.—Flowers normally remain up to 10 days on the plant.

Tepals:
- *Tepal color*.—Upon opening, the upper surface is Purple Group 75B with a central stripe Purple Group 75A. The lower surface is Purple Group 75B with a central stripe Yellow-White Group 158C. After opening the upper surface is a mix of Red Purple Group 75C and 75D with a central stripe of Red Purple Group 75A.
- *Quantity*.—Normally 6 tepals.
- *Size*.—About 55 mm in length by 35 mm wide.
- *Shape*.—Individual tepal shape is obovate. The tepal apex is acuminate. Tepal base is acute.
- *Apex recurvature*.—Strong.
- *Tepal cross section*.—Slightly cupped.
- *Margins*.—Entire. Medium undulations of margin observed.
- *Persistence*.—Tepals drop off cleanly.

Reproductive organs:
- *Pollen*.—None observed.
- *Anthers*.—Size: 4 mm in length. Color: Greyed-Yellow Group 160 A. Quantity: On average, 60.
- *Filaments*.—Color: Green Yellow 1D. Length: 8 mm.
- *Pistils*.—Quantity: On average, 45.
- *Stigmas*.—Inferior in location relative to the length of the filaments and the height of the anthers.
- *Styles*.—Color: Yellow Group 8D. Length: 13 mm.

Seed head characteristics: Seed not observed to date.

PLANT

Plant form: Climbing.

Plant growth: Compact.

Size: Seasons growth attains about 100 cm in height. Average spread is 50 cm.

Stems:
- *Color*.—Juvenile stems are Yellow-Green Group 144A. Mature stems are Yellow-Green Group 144A.
- *Internodes*.—On average, 55 mm between nodes.
- *Length*.—Normally 25 cm from the base of the plant to the flowering portion of the stem.
- *Diameter*.—About 3 mm.
- *Texture*.—Mature stems are ribbed.

Plant foliage:
- *Leaf characteristics*.—Deciduous.
- *Arrangement*.—Ternate.
- *Leaf size*.—Compound leaves are about 150 mm (l)× 150 mm (w). Leaflets are about 50 mm (l)×35 mm (w).
- *Abundance*.—On average 2 leaves per 10 cm of stem.
- *Leaflet color*.—Juvenile upper Yellow-Green Group 147A. Juvenile lower Yellow-Green Group 148D. Mature upper Yellow-Green Group 147A. Mature lower Yellow-Green Group 148D.
- *Stipules*.—Absent.
- *Petioles*.—Size: Normally 36 mm in length by 1.5 mm diameter. Texture: Smooth. Color: Yellow-Green Group 144A with intonations of Greyed-Orange Group 166A.

*Petioloule*.—Size: About 25 mm in length by 1 mm diameter. Texture: Smooth. Color: Yellow-Green Group 144A with intonations of Greyed- Orange Group 166A.

*Leaflet shape*.—Cordate. The base is rounded, apex acute or acuminate.

*Margin*.—Entire.

*Surface*.—The upper side is smooth, the lower side is smooth.

*Thickness*.—Moderate.

*Glossiness*.—Moderately glossy.

Disease resistance: Subject to any disease that normally attacks the species. However the variety is more tolerant to *Clematis* wilt, *Ascochyta clematidina*, than some *Clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *Clematis* plant named 'Evipo116', substantially as described and illustrated herein.

* * * * *

'Evipo116'

'Evipo116'